United States Patent [19]

Petry

[11] 4,001,059
[45] Jan. 4, 1977

[54] NITROGEN- AND FLUORINE-CONTAINING COMPOUNDS

[75] Inventor: Robert C. Petry, Huntsville, Ala.

[73] Assignee: Rohm and Haas Company, Philadelphia, Pa.

[22] Filed: May 24, 1963

[21] Appl. No.: 283,108

[52] U.S. Cl. .............................. 149/109.4; 149/42; 149/92; 149/119; 260/465.7
[51] Int. Cl.² ................. C06B 23/00; C07C 121/16
[58] Field of Search ............ 260/465.7; 149/109.4, 149/119

[56] References Cited

UNITED STATES PATENTS

| 3,539,617 | 11/1970 | Huskins et al. | 260/465.5 |
| 3,551,224 | 12/1970 | Huskins et al. | 149/18 |

*Primary Examiner*—Leland A. Sebastian

EXEMPLARY CLAIM

1. A compound selected from the group consisting of 1,2,3-tris(difluoroamino)-cyanopropane, 1-cyano-2,3,5,6-tetrakis(difluoramino)hexane, 1-cyano-2,3,6,7-tetrakis(difluoramino)heptane, and mixtures of 1-cyano-bis(difluoramino)pentenes.

5. Mixtures of 1-cyano-bis(difluoramino)pentenes.

5 Claims, No Drawings

NITROGEN- AND FLUORINE-CONTAINING COMPOUNDS

This invention concerns high molecular weight nitriles containing $NF_2$ groups. More specifically, it concerns high molecular weight nitriles which contain at least two $NF_2$ groupings.

These $NF_2$-containing nitriles are of particular interest as plasticizers for nitrocellulose and related compounds. They are of particular interest because they are high energy compounds, and thus do not detract from the explosive power of the nitrocellulose and related compounds as other plasticizers, such as dibutyl phthalate, tricresyl phosphate and dibutyl sebacate, do. They are also of very real interest as high energy plasticizers for compounds such as the esters of acrylic and methacrylic acid and $NF_2$-containing alcohols which are of particular interest as binders for propellant charges. In addition to the excellent physical properties of these esters, they have very high specific impulse.

The $NF_2$-containing nitriles of the present invention are prepared by reacting unsaturated high molecular weight nitriles with tetrafluorohydrazine, $N_2F_4$. The $N_2F_4$ adds across the double bond giving a bis(difluoramino) compound for each double bond in the high molecular weight nitriles.

Typical of the unsaturated nitriles which can be employed are:
3-cyanopropene,
2-cyano-3-difluoraminopropene,
1-cyano-2,5-hexadiene,
1-cyano-2,6-heptadiene, and
1-cyano-2,4-pentadiene.

On reaction with $N_2F_4$, these compounds give, respectively:
1-cyano-2,3-bis(difluoramino)propane,
1,2,3-tris(difluoramino)cyanopropane,
1-cyano-2,3,5,6-tetrakis(difluoramino)hexane,
1-cyano-2,3,6,7-tetrakis(difluoramino)heptane, and
mixtures of 1-cyano-bis(difluoramino)pentenes.

A typical reaction of 3-butene nitrile with tetrafluorohydrazine is described:

To a glass aerosol tube of 100 cc. capacity was introduced 6.7 grams (0.1 mole) 3-butene nitrile and 30.0 cc. carbon tetrachloride. The tube was placed on a high pressure manifold, degassed thoroughly under vacuum and finally flushed and degassed three times with nitrogen. Tetrafluorohydrazine was then introduced into the reactor tube to give an initial pressure of 80 psi. An initial pressure drop was due to absorption of tetrafluorohydrazine in the solvent. After recharging to 80 psi. with tetrafluorohydrazine, the mixture was heated to 92° C. During the next 10 hours, the tetrafluorohydrazine pressure was maintained between 83–44 psi. by recharging the system at frequent intervals. The total number of recharges was 23. The heating bath was lowered and after cooling the excess tetrafluorohydrazine was vented to the air. The reactor was then flushed with nitrogen and degassed three times after which air was introduced into the system which was then allowed to stand for fifteen minutes. The Aerosol tube with contents was removed from the manifold and poured into a 100 cc. flask and the solvent removed on a rotary stripper at reduced pressure. The residue weighed 16.92 grams and was identified as 3,4-bis(difluoramino)butyronitrile by infrared and n.m.r. $F^{19}$ spectral data and elemental analysis. The boiling point of 3,4-bis(difluoramino)butyronitrile is 58° C./1 mm., $N_D^{21.5}$ 1.3915.

Analysis Calculated for $C_4H_6F_4N_3$: % C, 28.05; % H, 2.94.
% F, 44.47; % N, 24.54.
Found: % C, 28.01; % H, 3.09.
% F, 44.36; % N, 25.43.

The preparation of the high molecular weight $NF_2$-containing nitriles of the present invention was conducted in solution at elevated temperatures and under pressure. As solvents, chloroform, methylene chloride, acetone and carbon tetrachloride have been employed. Any inert solvent for the unsaturated nitriles can be employed but carbon tetrachloride is particularly employed. The solvent-to-nitrile ratio is in the range of 10 to 1 to 10 to 3.

The reaction temperatures are in the range of 50° to 100° C., with the lowest possible temperature for reaction being employed. As indicated, the reaction products are high energy compounds and, therefore, it is desirable to maintain them at the lowest possible temperature at which they will be formed.

The pressures at which the reactions are conducted are not critical except that higher pressures force the reaction in the desired direction. Pressures of about 40 psi to about 100 psi can be employed.

Under the conditions noted hereinbefore, the reaction time will be about 5 to about 8 hours.

The details of the reaction of a series of high molecular weight nitriles with $N_2F_4$ are given in TABLE I which follows:

TABLE I

| ADDUCT | REACTION CONDITIONS | | | | | | CHARACTERIZATION DATA* Calculated/Found | | | |
|---|---|---|---|---|---|---|---|---|---|---|
| | Weight Olefin(g) | Time (Hrs.) | Temp. (° C.) | Pressure Range, psi. | Yield (g) | B.P. (° C.) | % C | % H | % F | % N |
| 1-Cyano-2,3-bis(difluoramino)propane | 6.7 | 12.5 | 92 | 35–80 | 11.53 | 58° C./1 mm. $N_D^{21.5}$ 1.3915 | 28.05 28.01 | 2.94 3.09 | 44.47 44.36 | 24.54 25.43 |
| 1,2,3-Tris(difluoramino)-2 cyanopropane | 2.3 | 1.75 | 100 | 39–100 | 3.16 | — | 21.53 22.03 | 2.26 2.39 | 51.10 50.20 | 25.11 25.31 |
| 1-Cyano-2,3,5,6-Tetrakis-(difluoramino)hexane | 3.2 | 6.50 | 92 | 40–98 | 7.20 | 88° C./0.8 mm. | 26.67 27.99 | 2.88 2.91 | 48.22 47.60 | 22.22 22.62 |
| 1-Cyano-2,3,6,7-Tetrakis-(difluoramino)heptane | 2.8 | 6.0 | 92 | 35–90 | 6.40 | — | 29.15 30.65 | 3.34 3.49 | 46.20 45.78 | 21.27 21.11 |
| Mixtures of 1-cyano-bis-(difluoramino)pentenes | 2.33 | 0.5 | 60 | 60 | 4.53 | — | 36.53 | 3.57 | 38.57 | 21.31 |

TABLE I-continued

| ADDUCT | REACTION CONDITIONS | | | | | | CHARACTERIZATION DATA* Calculated/Found | | | |
|---|---|---|---|---|---|---|---|---|---|---|
| | Weight Olefin(g) | Time (Hrs.) | Temp. (°C.) | Pressure Range, psi. | Yield (g) | B.P. (°C.) | % C | % H | % F | % N |
| | | 1.0 | 90 | 50 | | | 38.31 | 3.99 | 39.21 | 22.68 |

*Infrared and n.m.r. spectral data was also employed in product identification.

As set forth hereinbefore, these compounds are of interest as plasticizers for esters of acrylic and methacrylic acids and $NF_2$-containing alcohols. Typical of such esters is 2,3-bis(difluoramino)propyl acrylate. TABLE II sets forth a series of propellant compositions and the calculated specific impulse thereof:

TABLE II

Specific Impulse Calculations on Propellant Systems Containing Nitrile Adducts as Plasticizers (a) Nitrocellulose Systems

| % NC | % NFBN | % TNFCP | % NFCH | % AP | % RDX | % AL | Is |
|---|---|---|---|---|---|---|---|
| 15 | 30 | | | | 50 | 5 | 258.1 |
| 15 | 30 | | | | 45 | 10 | 259.1 |
| 10 | 30 | | | | 50 | 10 | 260.8 |
| 15 | 15 | | | 52.9 | | 17.1 | 266.7 |
| 20 | 20 | | | 47 | | 13 | 268.7 |
| 25 | 25 | | | 41.2 | | 8.8 | 267.9 |
| 30 | 30 | | | 35.6 | | 4.4 | 261.5 |
| 15 | | 15 | | 52.0 | | 18 | 266.3 |
| 20 | | 20 | | 45.9 | | 14.1 | 268.4 |
| 25 | | 25 | | 39.9 | | 10.1 | 269.6 |
| 30 | | 30 | | 33.9 | | 6.1 | 268.4 |
| 15 | | | 15 | 52.8 | | 17.2 | 267.2 |
| 20 | | | 20 | 46.9 | | 13.1 | 269.3 |
| 25 | | | 25 | 41 | | 9 | 269.1 |
| 30 | | | 30 | 35 | | 5 | 264.2 |
| 15 | 15 | | | 56.5 | | 13.5 | 269.1 |
| 20 | 20 | | | 51.9 | | 8.1 | 267.6 |
| 25 | 25 | | | 47 | | 3 | 258.3 |
| 15 | | 15 | | 55.7 | | 14.3 | 269.9 |
| 20 | | 20 | | 50.8 | | 9.2 | 271.0 |
| 25 | | 25 | | 45.9 | | 4.1 | 265.8 |
| 15 | | | 15 | 56.5 | | 13.5 | 269.7 |
| 20 | | | 20 | 51.9 | | 8.1 | 268.5 |
| 25 | | | 25 | 47 | | 3 | 260.5 |

NOTE:
NFPA - 2,3-bis(difluoramino)propyl acrylate
NFBN - 3,4-bis(difluoramino)butyronitrile
TNFCP - 1,2,3-tris(difluoramino)-2-cyanopropane
NFCH - 3,4,6,7-tetrakis-difluoramino heptanenitrile
AP - Ammonium perchlorate
Al - Aluminum It should be noted that the specific impulse in all cases is high, being considerably in excess of 250 in all cases.

I claim:

1. A compound selected from the group consisting of 1,2,3-tris(difluoramino)-cyanopropane, 1-cyano-2,3,5,6-tetrakis(difluoramino)hexane, 1-cyano-2,3,6,7-tetrakis(difluoramino)heptane, and mixtures of 1-cyano-bis(difluoramino)pentenes.
2. 1,2,3-Tris(difluoramino)cyanopropane.
3. 1-Cyano-2,3,5,6-tetrakis(difluoramino)hexane.
4. 1-Cyano-2,3,6,7-tetrakis(difluoramino)heptane.
5. Mixtures of 1-cyano-bis(difluoramino)pentenes.

* * * * *